US008147539B2

(12) United States Patent
McMorrow et al.

(10) Patent No.: US 8,147,539 B2
(45) Date of Patent: Apr. 3, 2012

(54) STENT WITH A COATING FOR DELIVERING A THERAPEUTIC AGENT

(75) Inventors: David McMorrow, Galway (IE); Robert Nolan, Knocknacarra (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 401 days.

(21) Appl. No.: 11/953,973

(22) Filed: Dec. 11, 2007

(65) Prior Publication Data

US 2008/0215139 A1     Sep. 4, 2008

Related U.S. Application Data

(60) Provisional application No. 60/876,485, filed on Dec. 20, 2006.

(51) Int. Cl.
*A61F 2/06* (2006.01)
(52) U.S. Cl. ............... 623/1.46; 623/1.42; 623/1.43; 623/1.44; 623/1.45
(58) Field of Classification Search ............ 623/1.1, 623/1.42–1.46, 1.13
See application file for complete search history.

(56) References Cited

U.S. PATENT DOCUMENTS

| 4,655,771 A | 4/1987 | Wallsten |
| 4,954,126 A | 9/1990 | Wallsten |
| 5,061,275 A | 10/1991 | Wallsten et al. |
| 5,449,373 A | 9/1995 | Pinchasik et al. |
| 5,591,227 A | 1/1997 | Dinh et al. |
| 5,697,967 A | 12/1997 | Dinh et al. |
| 5,733,327 A | 3/1998 | Igaki et al. |
| 5,762,638 A | 6/1998 | Shikani et al. |
| 5,779,729 A * | 7/1998 | Severini ............... 623/1.15 |
| 5,833,651 A | 11/1998 | Donovan et al. |
| 5,837,313 A | 11/1998 | Ding et al. |
| 5,897,955 A | 4/1999 | Drumheller |
| 5,914,182 A | 6/1999 | Drumheller |
| 5,980,972 A | 11/1999 | Ding |
| 5,981,568 A | 11/1999 | Kunz et al. |
| 5,997,468 A | 12/1999 | Wolff et al. |
| 6,042,875 A | 3/2000 | Ding et al. |
| 6,099,562 A | 8/2000 | Ding et al. |
| 6,120,536 A | 9/2000 | Ding et al. |
| 6,153,252 A | 11/2000 | Hossainy et al. |

(Continued)

FOREIGN PATENT DOCUMENTS

EP    1479401    11/2004

(Continued)

OTHER PUBLICATIONS

U.S. Appl. No. 60/876,485, filed Dec. 20, 2006, Inventor McMorrow et al.

*Primary Examiner* — David Isabella
*Assistant Examiner* — Yashita Sharma
(74) *Attorney, Agent, or Firm* — Vidas, Arrett & Steinkraus, P.A.

(57) ABSTRACT

The invention relates generally to a medical device for delivering a therapeutic agent to the body tissue of a patient, and methods for making such a medical device. More particularly, the invention is directed to a stent, such as an intravascular stent, having an inner and outer coating compositions disposed thereon. In another embodiment, the inner coating composition and outer coating composition are separated by a barrier coating composition.

8 Claims, 10 Drawing Sheets

U.S. PATENT DOCUMENTS

| | | |
|---|---|---|
| 6,228,845 B1 | 5/2001 | Donovan et al. |
| 6,258,121 B1 | 7/2001 | Yang et al. |
| 6,316,018 B1 | 11/2001 | Ding et al. |
| 6,358,556 B1 | 3/2002 | Ding et al. |
| 6,545,097 B2 | 4/2003 | Pinchuk et al. |
| 6,569,195 B2 | 5/2003 | Yang et al. |
| 6,660,034 B1 | 12/2003 | Mandrusov et al. |
| 6,855,770 B2 | 2/2005 | Pinchuk et al. |
| 6,899,731 B2 | 5/2005 | Li et al. |
| 6,918,929 B2 | 7/2005 | Udipi et al. |
| 6,939,376 B2 | 9/2005 | Shulze et al. |
| 6,979,348 B2 | 12/2005 | Sundar |
| 7,014,654 B2 | 3/2006 | Welsh et al. |
| 7,055,237 B2 | 6/2006 | Thomas |
| 7,063,884 B2 | 6/2006 | Hossainy et al. |
| 7,105,175 B2 | 9/2006 | Schwarz |
| 7,135,038 B1 | 11/2006 | Limon |
| 7,144,419 B2 | 12/2006 | Cheng et al. |
| 7,144,422 B1 | 12/2006 | Rao |
| 7,156,869 B1 | 1/2007 | Pacetti |
| 7,279,175 B2 | 10/2007 | Chen et al. |
| 7,288,084 B2 | 10/2007 | Li |
| 7,318,945 B2 | 1/2008 | Thornton et al. |
| 2003/0225450 A1 | 12/2003 | Shulze et al. |
| 2004/0024450 A1 | 2/2004 | Shulze et al. |
| 2004/0030380 A1 | 2/2004 | Shulze et al. |
| 2004/0059409 A1 | 3/2004 | Stenzel |
| 2004/0230298 A1 | 11/2004 | Udipi et al. |
| 2005/0033414 A1 | 2/2005 | Zhang et al. |
| 2005/0038505 A1 | 2/2005 | Shulze et al. |
| 2005/0043788 A1 | 2/2005 | Luo et al. |
| 2005/0070997 A1 | 3/2005 | Thornton et al. |
| 2005/0084515 A1 | 4/2005 | Udipi et al. |
| 2005/0187611 A1 | 8/2005 | Ding et al. |
| 2005/0208200 A1 | 9/2005 | Ding et al. |
| 2005/0287184 A1 | 12/2005 | Hossainy et al. |
| 2006/0088654 A1 | 4/2006 | Ding et al. |
| 2006/0224234 A1 | 10/2006 | Jayaraman |
| 2006/0229706 A1 | 10/2006 | Shulze et al. |
| 2007/0178136 A1 | 8/2007 | Arney et al. |
| 2007/0282422 A1 * | 12/2007 | Biggs et al. .................. 623/1.13 |
| 2007/0298069 A1 | 12/2007 | Bucay-Couto et al. |
| 2008/0015676 A1 | 1/2008 | Kantor |

FOREIGN PATENT DOCUMENTS

| | | |
|---|---|---|
| WO | 9416646 | 8/1994 |
| WO | 9856312 | 12/1998 |
| WO | 0178626 | 10/2001 |
| WO | 0226139 | 4/2002 |
| WO | 2006052574 | 5/2006 |
| WO | 2006065685 | 6/2006 |

* cited by examiner

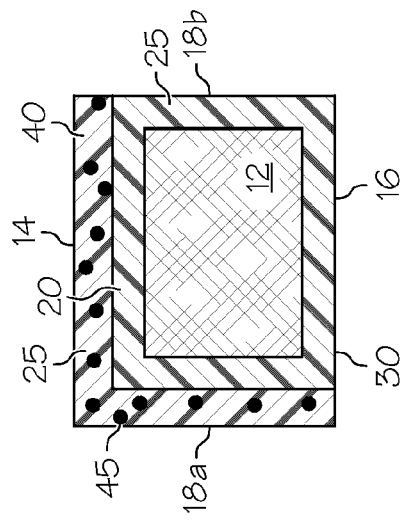
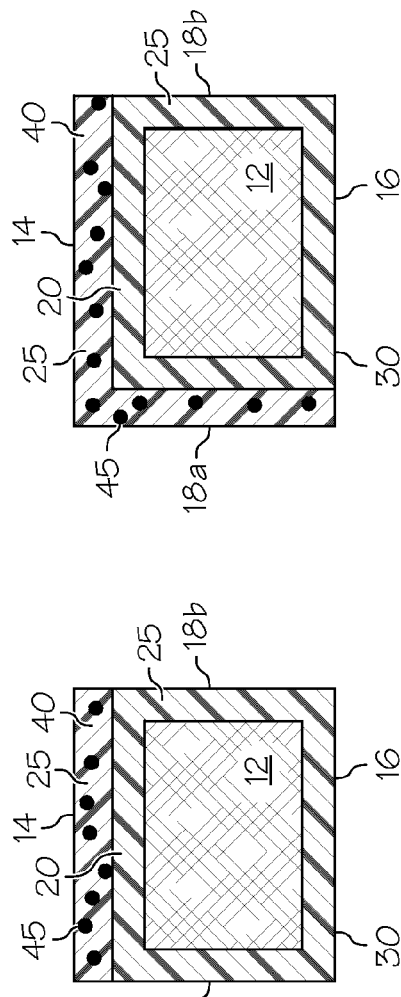
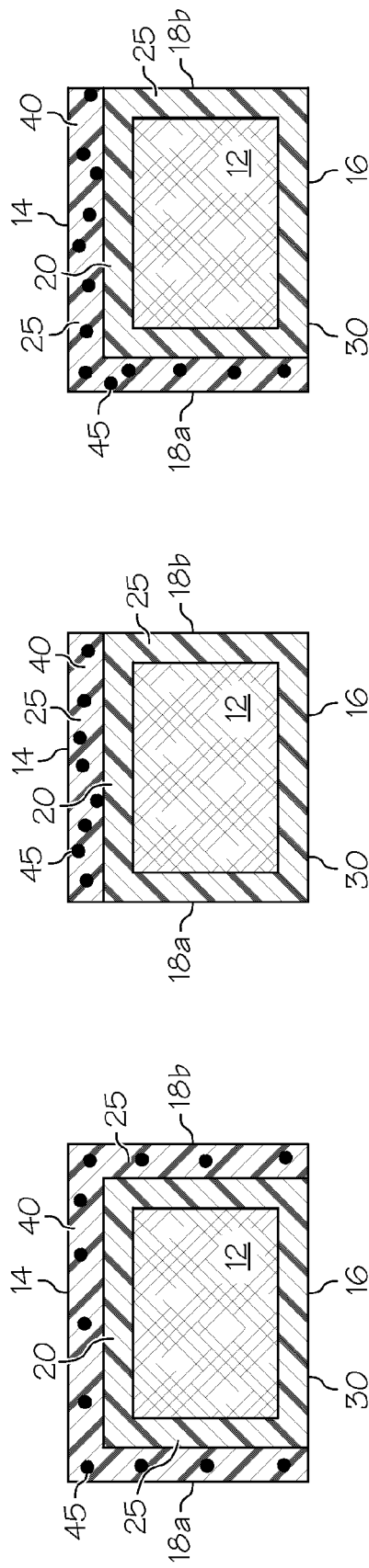
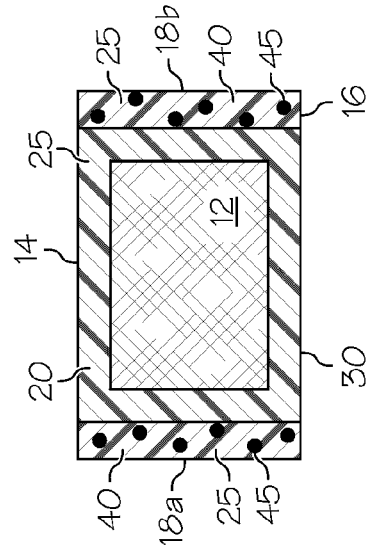
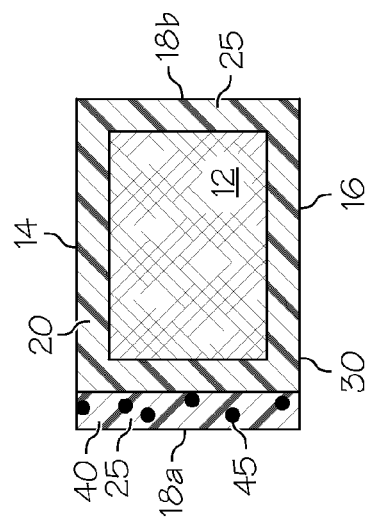

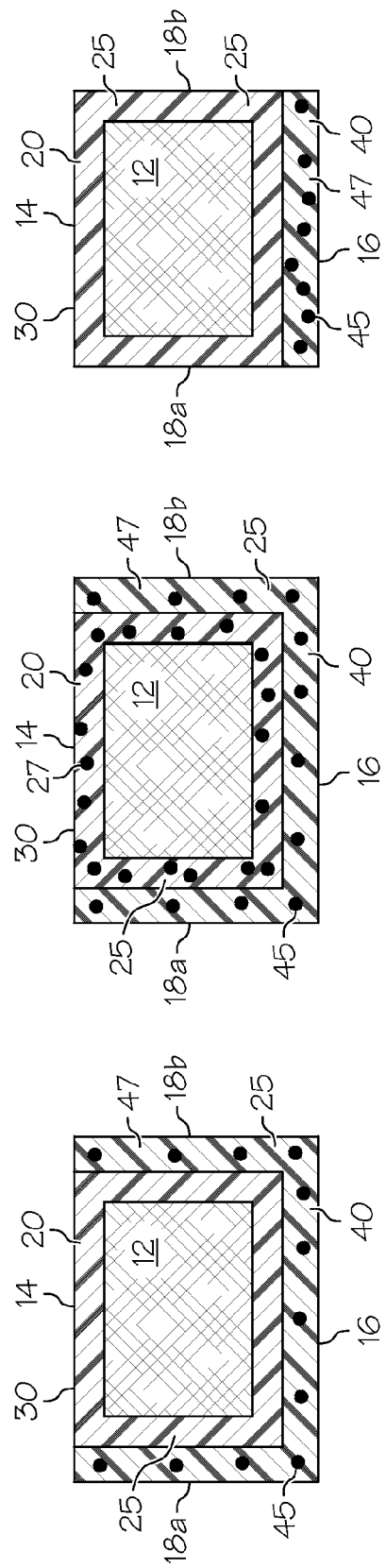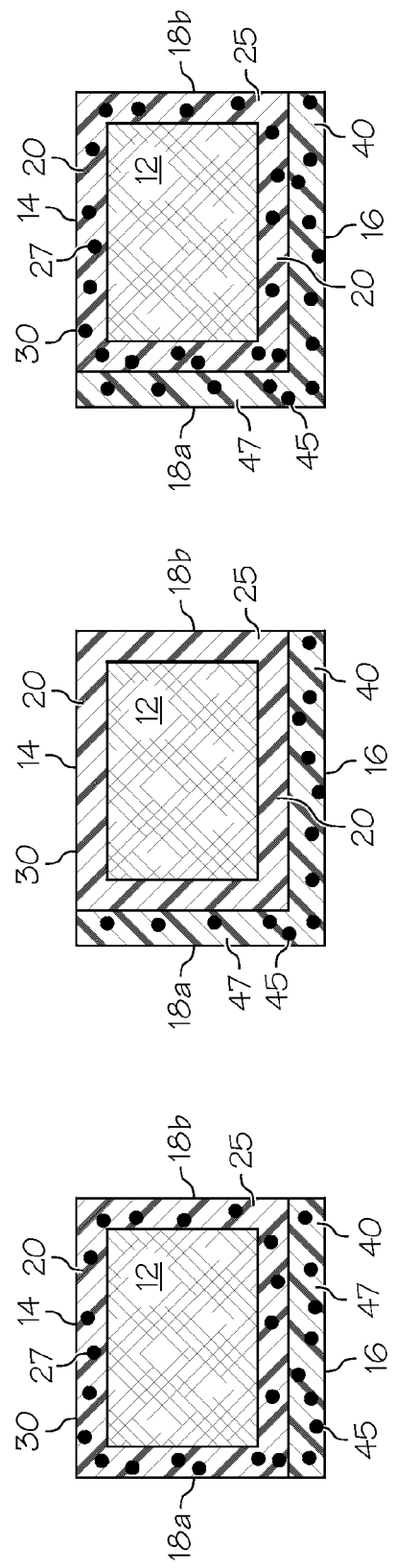

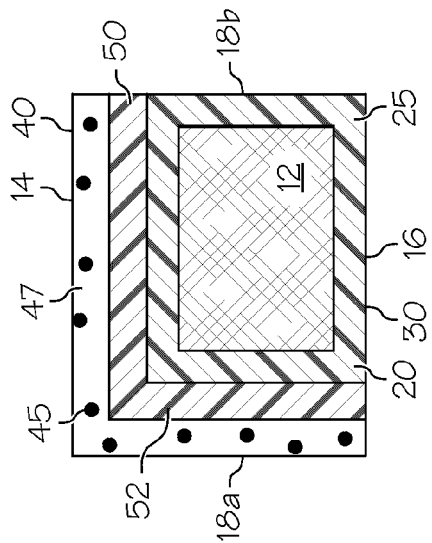
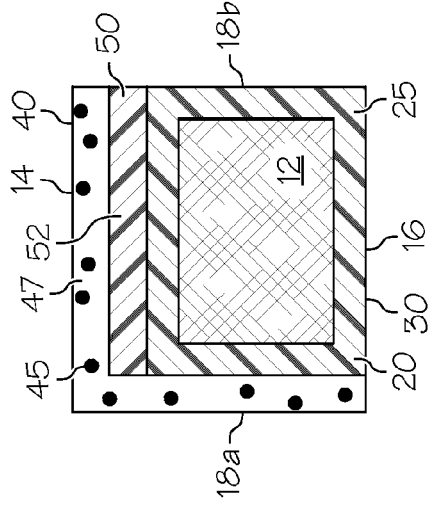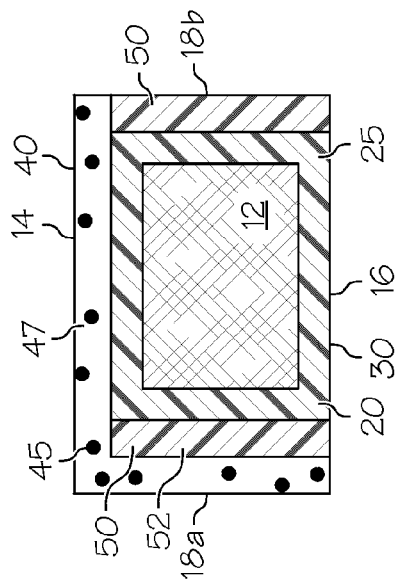
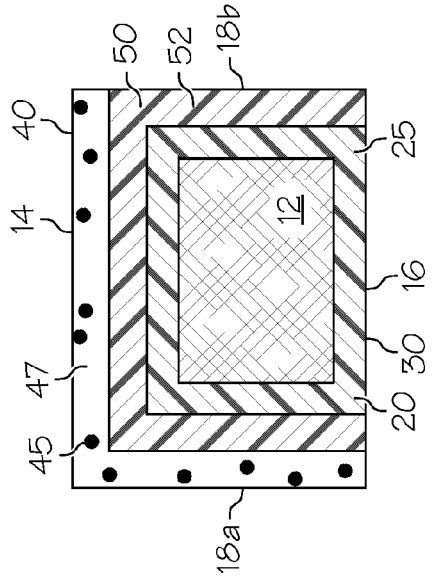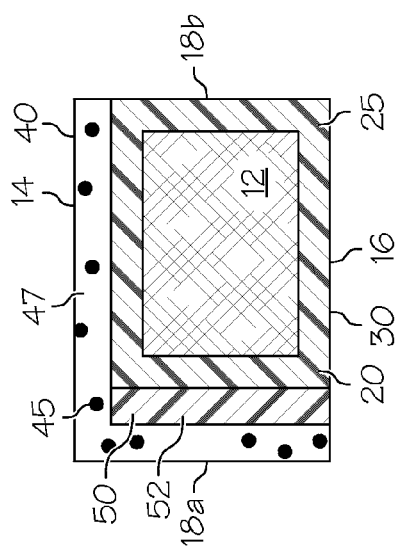

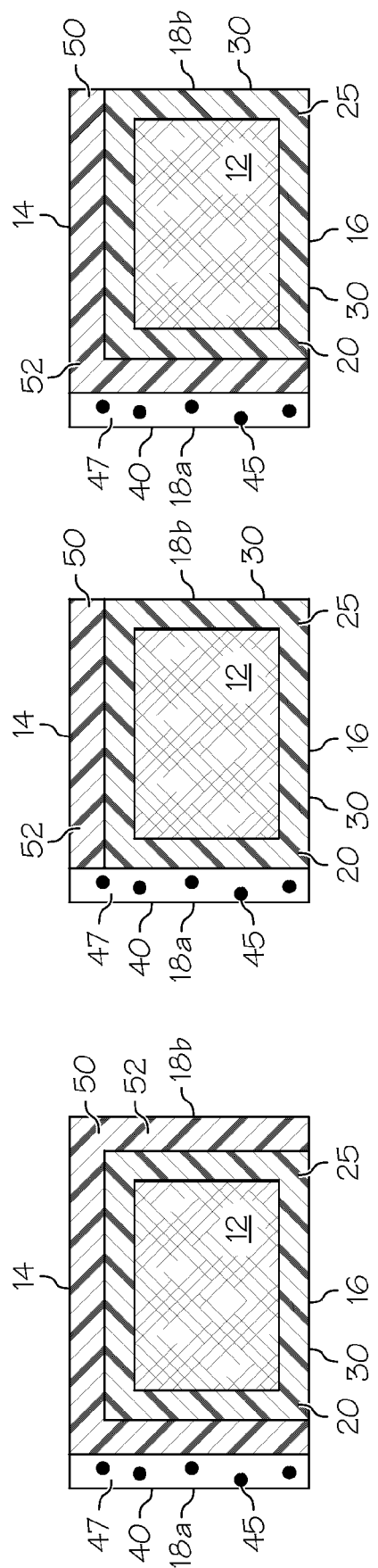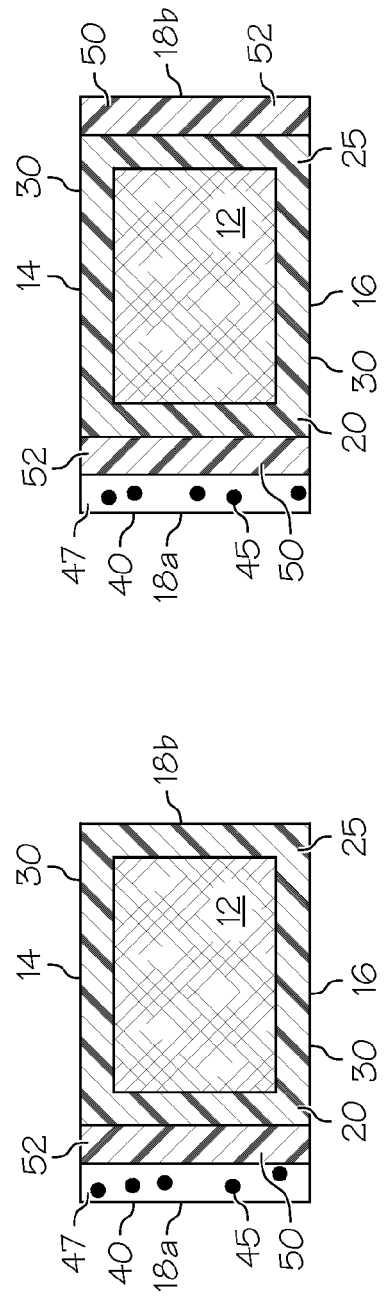

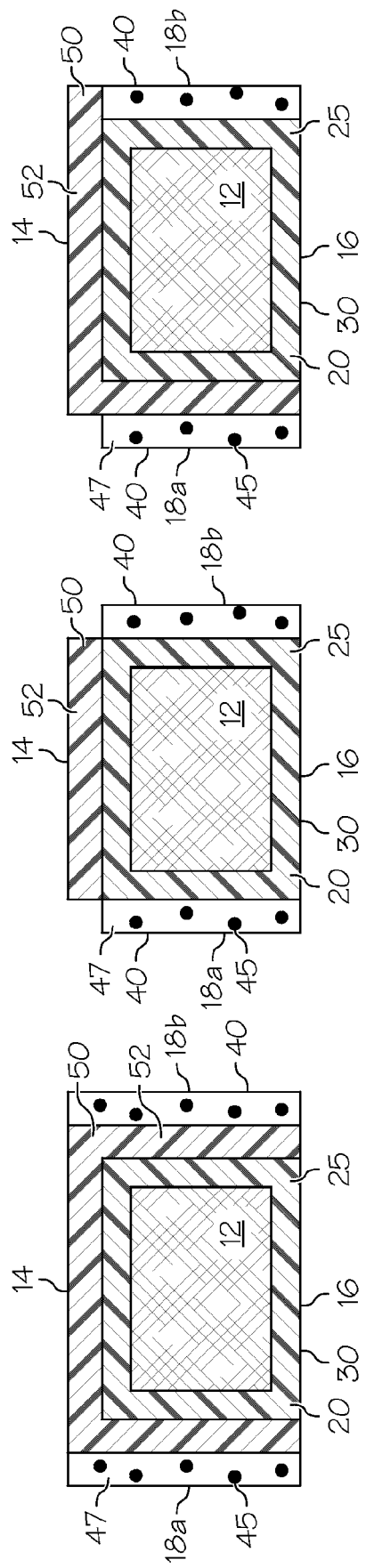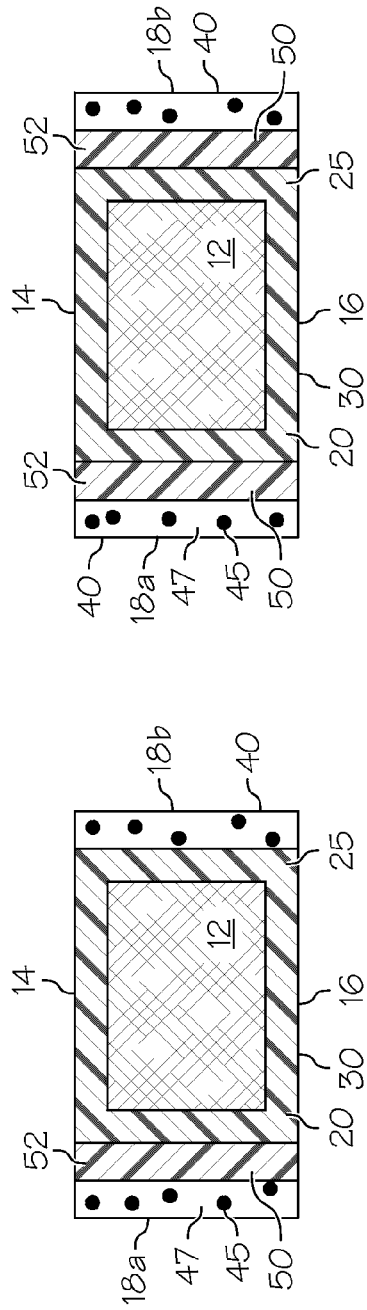

STENT WITH A COATING FOR DELIVERING A THERAPEUTIC AGENT

This application claims priority to U.S. Provisional Application No. 60/876,485, filed Dec. 20, 2006.

FIELD OF THE INVENTION

The invention relates generally to a medical device for delivering a therapeutic agent to the body tissue of a patient, and methods for making such a medical device. More particularly, the invention is directed to a stent, such as an intravascular stent, having an inner and outer coating compositions disposed thereon. In another embodiment, the inner coating composition and outer coating composition are separated by a barrier coating composition.

BACKGROUND OF THE INVENTION

Medical devices, such as implantable stents, have been coated with coating compositions comprising a therapeutic agent. One method of forming such coatings is to apply a coating composition containing a therapeutic agent to all the surfaces of the medical device. For example, for stents comprising a plurality of struts, all of the surfaces of the struts are coated with the coating composition to form a coating that encapsulates each of the struts. A reason for coating all the surfaces of the struts is to ensure that the coating remains on the struts by having the coating wrap around the struts.

In many medical devices, however, all of the surfaces of the medical device do not need to be coated with a coating composition comprising a therapeutic agent. For instance, in an intravascular stent, the inner or luminal surface of the strut may not have to be coated with a coating composition containing a therapeutic agent which is useful for treating the blood vessel wall, such as an anti-restenosis agent. This is because the luminal surfaces of the struts do not generally come in direct contact with the blood vessel wall to which the therapeutic agent is directed. Therefore, it is not necessary to coat the luminal surfaces of the struts with a coating composition containing such a therapeutic agent. The application of the coating to surfaces that do not need to be coated can result in undesired exposure of the patient to the therapeutic agent as well as increased costs of manufacturing the coated medical device associated with such increased use of the therapeutic agent.

Accordingly, there is a need for medical devices, such as stents, having coatings containing a therapeutic agent that sufficiently remain on the devices as well as coatings that reduce the undesired exposure of the patient to unnecessary amounts of therapeutic agents and that reduce the costs of manufacturing coated medical devices.

SUMMARY

These and other objectives are addressed by the present invention. The present invention provides a coating containing a therapeutic agent that can be applied to all surfaces of the medical device so that the coating can sufficiently remain on the medical device. Also, the coating allows the therapeutic agent to be targeted to specific body tissue, thereby reducing undesired exposure to the therapeutic agent as well as reducing the manufacturing costs associated with using unnecessary amounts of the therapeutic agent.

In one embodiment, the present invention comprises a stent for implantation in a body lumen of a patient. The stent comprises a stent sidewall structure comprising a plurality of struts. At least one strut has an abluminal surface, a luminal surface opposite the abluminal surface, a first side surface, and a second side surface opposite the first side surface, in which the first and second side surfaces are each adjacent to and connect the abluminal surface and the luminal surface. The stent can comprise one or more compositions. For example, there is an inner coating composition comprising a first polymer disposed on the abluminal surface, luminal surface, first and second side surfaces and any other surface of the strut such that the inner coating composition is disposed on all surfaces of the strut. The inner coating composition is free of a therapeutic agent when applied onto the surfaces of the strut. The inner coating composition that is disposed on the luminal surface forms an exposed surface. Besides the inner coating composition, there is an outer coating composition disposed on at least a portion of the inner coating composition that is disposed on at least one of the abluminal surface or first side surface or second side surface. The outer coating composition comprises a first therapeutic agent and the first polymer.

In another embodiment, the stent comprises a stent sidewall structure comprising a plurality of struts in which at least one strut has an abluminal surface, a luminal surface opposite the abluminal surface, a first side surface, and a second side surface opposite the first side surface. The first and second side surfaces are each adjacent to and connect the abluminal surface and the luminal surface. An inner coating composition comprising a first polymer is disposed on the abluminal surface, luminal surface, first and second side surfaces and any other surface of the strut such that the inner coating composition is disposed on all surfaces of the strut. The inner coating composition that is disposed on the abluminal surface forms an exposed surface. An outer coating composition is disposed on at least a portion of the inner coating composition that is disposed on the luminal surface, wherein the outer coating composition comprises a first therapeutic agent and a second.

In addition, in other embodiments, the stent comprises a stent sidewall structure comprising a plurality of struts in which at least one strut has an abluminal surface, a luminal surface opposite the abluminal surface, a first side surface, and a second side surface opposite the first side surface. The first and second side surfaces are each adjacent to and connect the abluminal surface and the luminal surface. An inner coating composition comprising a first polymer is disposed on the abluminal surface, luminal surface, first and second side surfaces and any other surface of the strut such that the inner coating composition is disposed on all surfaces of the strut. Also, the inner coating composition that is disposed on the luminal surface forms an exposed surface. Furthermore, a barrier coating composition comprising a second polymer is disposed on at least a portion of the inner coating composition that is disposed on at least one of the abluminal surface or first side surface or second side surface. The barrier coating composition is free of a therapeutic agent when applied onto the inner coating composition. An outer coating composition is disposed on at least a portion of the barrier coating composition that is disposed on the portion of the inner coating composition disposed on at least one of the abluminal surface or first side surface or second side surface. The outer coating composition comprises a first therapeutic agent and a third polymer.

In yet another embodiment, the stent comprises a stent sidewall structure comprising a plurality of struts in which at least one strut has an abluminal surface, a luminal surface opposite the abluminal surface, a first side surface, and a second side surface opposite the first side surface. The first and second side surfaces are each adjacent to and connect the abluminal surface and the luminal surface. An inner coating composition comprising a first polymer is disposed on the abluminal surface, luminal surface, first and second side surfaces and any other surface of the strut such that the inner coating composition is disposed on all surfaces of the strut. The inner coating composition that is disposed on the abluminal surface forms an exposed surface. A barrier coating composition comprising a second polymer disposed on at least a portion of the inner coating composition that is disposed on at least one of the luminal surface or first side surface or second side surface. The barrier coating composition is free of a therapeutic agent when applied onto the inner coating composition. An outer coating composition disposed on at least a portion of the barrier coating composition that is disposed on the portion of the inner coating composition disposed on at least one of the luminal surface or first side surface or second side surface. The outer coating composition comprises a first therapeutic agent and a third polymer.

BRIEF DESCRIPTION OF THE DRAWINGS

FIGS. 2A-2E show cross-sectional views of embodiments of a stent strut having an inner and an outer coating composition disposed on one or more of the strut surfaces.

FIGS. 3A-3F show cross-sectional views of additional embodiments of a stent strut having an inner and an outer coating composition disposed on one or more of the strut surfaces.

DETAILED DESCRIPTION

Figure 1:
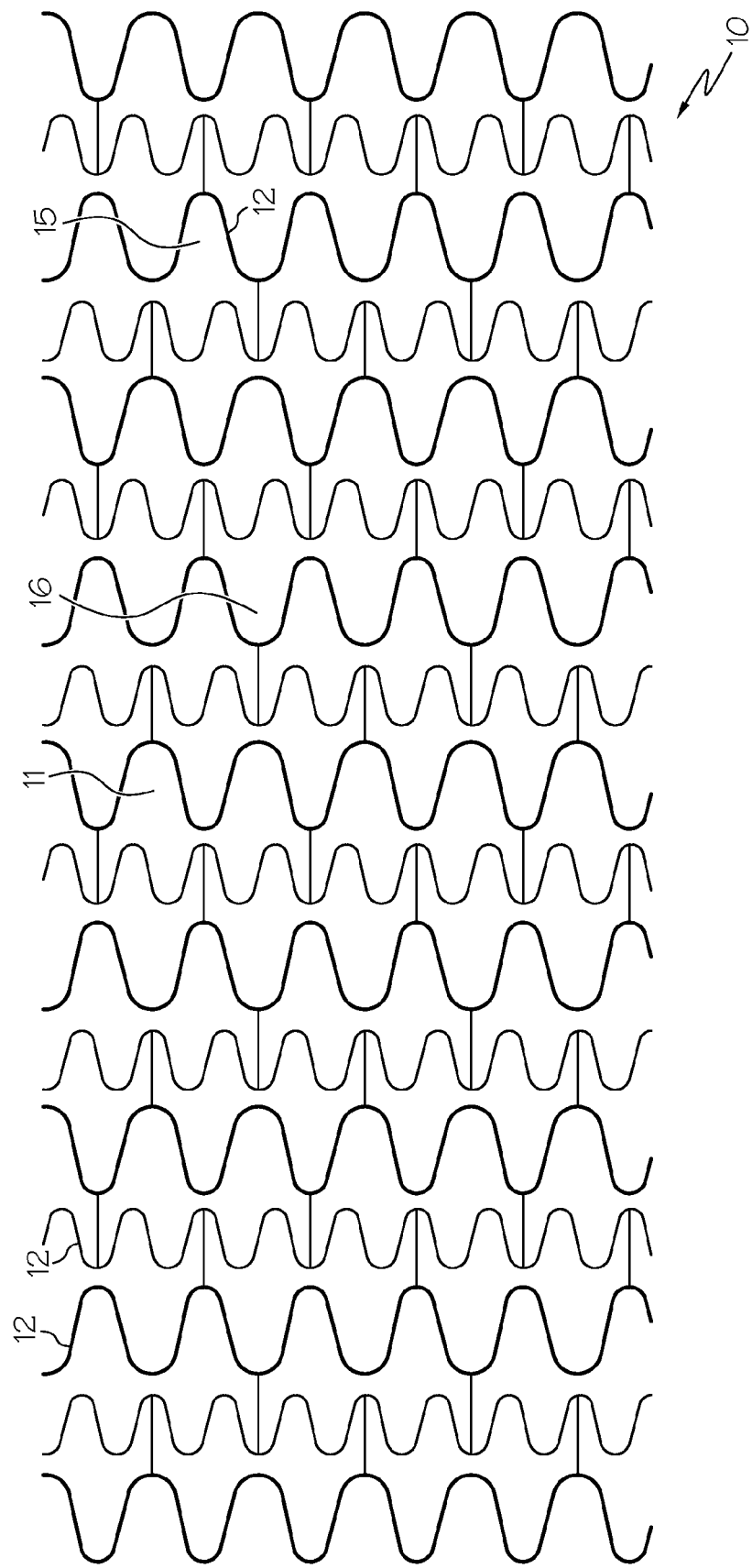
FIG. 1 depicts a perspective view of an intravascular stent comprising a plurality of struts.

FIG. 1 shows an example of a stent that is suitable for use in the present invention. Additional suitable stents are discussed below. FIG. 1 shows an intravascular stent 10 comprising a sidewall 11, which comprises a plurality of struts 12 and at least one opening 15 in the sidewall 11. Generally, the openings 15 are disposed between adjacent struts 12. This embodiment is an example of a stent where the struts and openings of the stent define a sidewall stent structure having openings therein. Also, the sidewall 11 may have a first sidewall surface. The first sidewall surface 16 in this figure is an outer sidewall surface or abluminal surface, which faces the body lumen wall when the stent is implanted. Opposite the first sidewall surface 16, which is not show in FIG. 1, is an inner sidewall surface or luminal surface, which faces away from the body lumen wall.

Figure 1A:
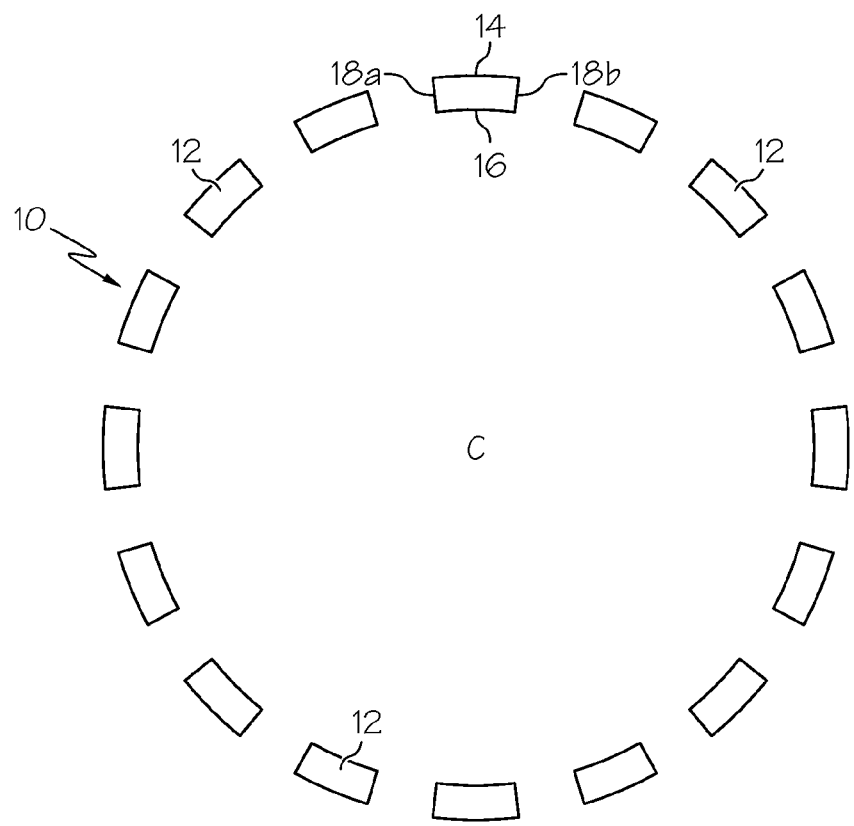
FIG. 1A shows a cross-sectional view of the stent of FIG. 1.

FIG. 1A depicts a cross-section of the stent 10 of FIG. 1. Generally, each individual strut 12 has an outer surface or abluminal surface 14, an inner surface or luminal surface 16 that is opposite the abluminal surface 14 and at least one side surface. The struts in FIG. 1A have a first side surface 18a and second side surface 18b, which is opposite the first side surface 18a. The abluminal surface 14 of the strut 12 is the surface that directly faces the body lumen wall when the stent is implanted. The abluminal surface 14 need not include only one flat surface or facet. Instead, it can be rounded, such as in the case of a wire strut 12, or have a number of facets. The luminal surface 16 of the strut 12 is the surface that is opposite the abluminal surface 14 and faces the center C of the stent 10. In this stent, the two side surfaces 18a and 18b are the surfaces of the strut 12 that are each adjacent to and connect of the abluminal surface 14 and the luminal surface 16. Like the abluminal surface 14, the luminal surface 16 and side surfaces 18a and 18b can be rounded or have a number of facets.

Figure 1B:
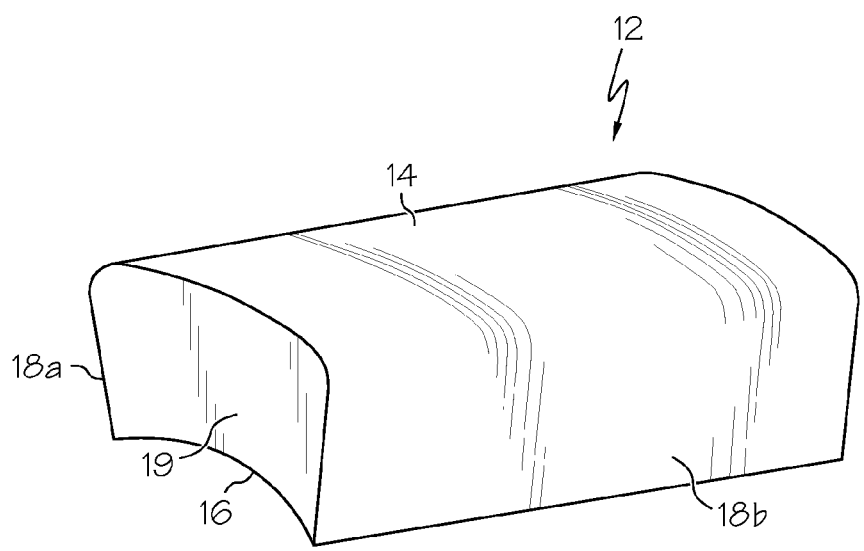
FIG. 1B shows a peripheral view of a segment of a strut 12 that has been cut from of the stent 10 shown in FIG. 1.

FIG. 1B is a peripheral view of a segment of a strut 12 that has been cut from the stent 10 depicted in FIG. 1. This segment has a cut surface 19. The strut has an abluminal surface 14, a luminal surface 16 and first and second side surfaces 18a and 18b. Each of these surfaces is an exposed surface of the strut 12 since they are each not covered by another material, such as a coating composition.

FIGS. 2A-2E show cross-sectional views of embodiments where an inner coating composition 20, is disposed on all surfaces of a stent strut 12. The inner coating composition 20 disposed on the luminal surface 16 of the strut 12 forms an exposed surface 30. An outer coating composition 40 is disposed on a portion of the inner coating composition 20.

As shown in FIG. 2A, in certain embodiments, an inner coating composition 20, comprising a first polymer 25, is disposed on the abluminal surface 14, luminal surface 16, and first, second side surfaces 18a, 18b and any other surface of the strut 12. The inner coating composition 20 is disposed on all surfaces of the strut 12 thereby encapsulating the strut 12. Preferably, as shown in FIG. 2A, the inner coating composition 20 is disposed directly on the strut surfaces so that there is no intervening material between the inner coating composition 20 and the strut surfaces. Also, in this embodiment, the inner coating composition 20 is free of a therapeutic agent when applied onto the abluminal surface 14, luminal surface 16 and first and second side surfaces 18a, 18b. In addition, as shown in FIG. 2A, the inner coating composition 20 that is disposed on the luminal surface 14 of the strut 12 forms an exposed surface 30 that is not covered by another coating composition.

Furthermore, in FIG. 2A, an outer coating composition 40, which comprises a first therapeutic agent 45 and the first polymer 20, is disposed on portions of the inner coating composition 20 that are disposed on the abluminal surface 14 and the first and second side surfaces 18a, 18b of the strut 12. The luminal surface 16 of the strut 12 is free of the outer coating composition 40. Preferably, as shown in FIG. 2A, the outer coating composition 40 is disposed directly on the inner coating composition 20 so that there is no intervening material between the inner and outer coating compositions 20, 40. The outer coating composition 40 can be disposed on the inner coating composition 20 such that only a part of or the entire inner coating composition 20 disposed on each of these surfaces is covered by the outer coating composition 40. Preferably, the first therapeutic agent 45 is one for treating the body lumen wall, such as an anti-restenosis agent. Also, when the outer coating composition 40 is applied to the inner coating composition 20, some of the therapeutic agent 45 can migrate into the inner coating composition 20.

The embodiment shown in FIG. 2B is similar to that shown in FIG. 2A except that the outer coating composition 40 is only disposed on a portion of the inner coating composition 20 that is disposed on the abluminal surface 14 of the strut 12. The outer coating composition 40 is not disposed on the inner coating composition 20 that is disposed on either of the side surfaces 18a, 18b.

FIG. 2C shows an embodiment similar to that shown in FIG. 2A except that the outer coating composition 40 is only disposed on a portion of the inner coating composition 20 that is disposed on the abluminal surface 14 and on a portion of the inner coating composition 20 that is disposed on one of the side surfaces 18a. The outer coating composition 40 is not disposed on the inner coating composition 20 that is disposed on the other side surface 18b. Alternatively, the outer coating composition 40 can be disposed on the inner coating composition 20 that is disposed on side surface 18b instead of that disposed on side surface 18a.

FIG. 2D shows an embodiment similar to that shown in FIG. 2A except that the outer coating composition 40 is only disposed on a portion of the inner coating composition 20 that is disposed on one of the side surfaces 18a. The outer coating composition 40 is not disposed on the inner coating composition 20 that is disposed on the abluminal surface 14, adluminal surface 16 or the other side surface 18b. Alternatively, the outer coating composition 40 can be disposed on the inner coating composition 20 that is disposed on side surface 18b instead of that disposed on side surface 18a. Also, as shown in FIG. 2E, the outer coating composition 40 can be disposed on portions of both the inner coating composition 20 that is disposed on both side surfaces 18a, 18b.

FIGS. 3A-3F show cross-sectional views of embodiments where an inner coating composition 20 is disposed on all surfaces of a stent strut 12. The inner coating composition 20 disposed on the abluminal surface 14 of the strut 12 forms an exposed surface 30. An outer coating composition 40 comprising a therapeutic agent 45 is disposed on a portion of the inner coating composition 20.

As shown in FIG. 3A, in certain embodiments, an inner coating composition 20, comprising a first polymer 25, is disposed on the abluminal surface 14, luminal surface 16, first and second side surfaces 18a, 18b and any other surface of the strut 12. The inner coating composition 20 is disposed on all surfaces of the strut 12 thereby encapsulating the strut 12. Preferably, as shown in this figure, the inner coating composition 20 is disposed directly on the strut surfaces so that there is no intervening material between the inner coating composition 20 and the strut surfaces. Also, in this embodiment, the inner coating composition 20 is free of a therapeutic agent when applied onto the abluminal surface 14, luminal surface 16 and first and second side surfaces 18a, 18b of the strut 12. In addition, as shown in FIG. 3A, the inner coating composition 20 that is disposed on the abluminal surface 14 of the strut 12 forms an exposed surface 30 that is not covered by another coating composition.

Furthermore, in FIG. 3A, an outer coating composition 40, which comprises a first therapeutic agent 45 and the second polymer 47, is disposed on a portion of the inner coating composition 20 that is disposed on the luminal surface 16 and on a portion of the inner coating composition 20 disposed on the first and second side surfaces 18a, 18b of the strut 12. Preferably, as shown in FIG. 3A, the outer coating composition 40 is disposed directly on the inner coating composition 20 so that there is no intervening material between the inner and outer coating compositions 20, 40. The outer coating composition 40 can be disposed on the inner coating composition 20 such that only a part of or the entire inner coating composition 20 disposed on each of these surfaces is covered by the outer coating composition 40. Preferably, the first therapeutic agent 45 is one for delivery to a body fluid such as blood. Also, when the outer coating composition 40 is applied to the inner coating composition 20, it is possible some of the therapeutic agent 45 can migrate into the inner coating composition 20. The first and second polymers 25, 47 can be the same or different.

FIG. 3B shows an embodiment similar to that shown in FIG. 3A except that the inner coating composition 20 comprises a second therapeutic agent 27. Preferably, the second therapeutic agent 27 is suitable for treating the body lumen wall, such as an anti-restenosis agent.

The embodiment shown in FIG. 3C is similar to that shown in FIG. 3A except that the outer coating composition 40 is only disposed on a portion of the inner coating composition 20 that is disposed on the luminal surface 16 of the strut 12. The outer coating composition 40 is not disposed on the inner coating composition 20 that is disposed on either of the side surfaces 18a, 18b. FIG. 3D depicts an embodiment similar to that shown in FIG. 3C except that the inner coating composition 20 comprises a second therapeutic agent 27.

The embodiment shown in FIG. 3E is similar to that shown in FIG. 3A except that the outer coating composition 40 is disposed on a portion of the inner coating composition 20 that is disposed on the luminal surface 16 of the strut 12 and disposed on a portion of the inner coating composition 20 that is disposed on the one of the side surfaces 18s. The outer coating composition 40 is not disposed on the inner coating composition 20 that is disposed on side surface 18b. In an alternative embodiment, the outer coating composition 40 is disposed on a portion of the inner coating composition 20 that is disposed on side surface 18b, instead of on side surface 18a. FIG. 3F depicts an embodiment similar to that shown in FIG. 3E except that the inner coating composition 20 comprises a second therapeutic agent 27.

Figure 4C:
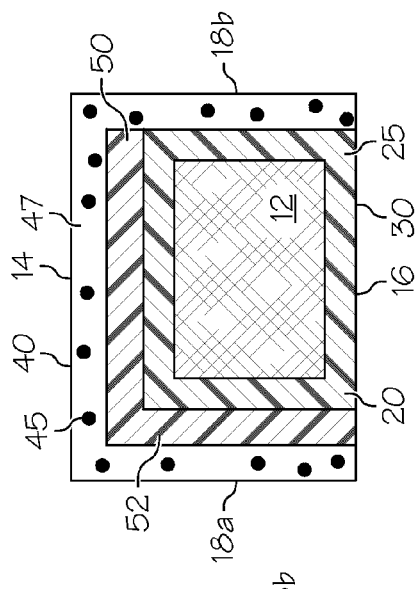
FIGS. 4A-4Y show cross-sectional views of embodiments of a stent strut having an inner coating composition, barrier coating composition and an outer coating composition disposed on one or more of the strut surfaces.
Figure 4B:
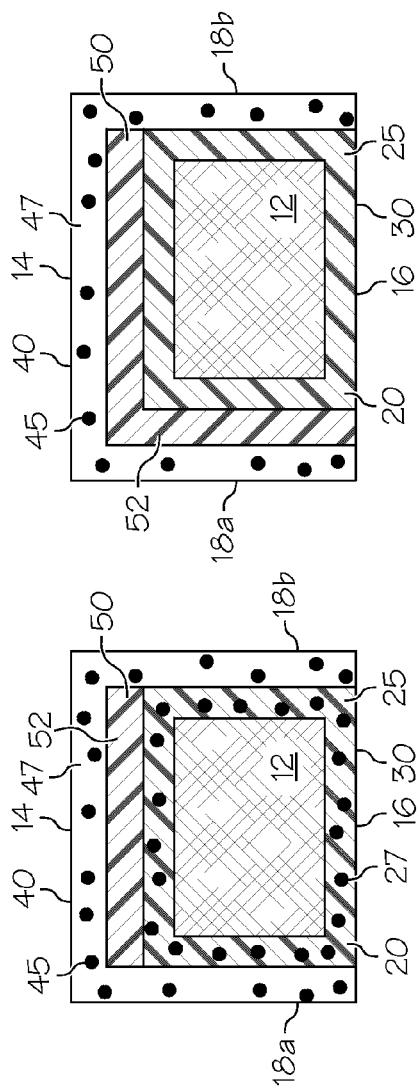
Figure 4A:
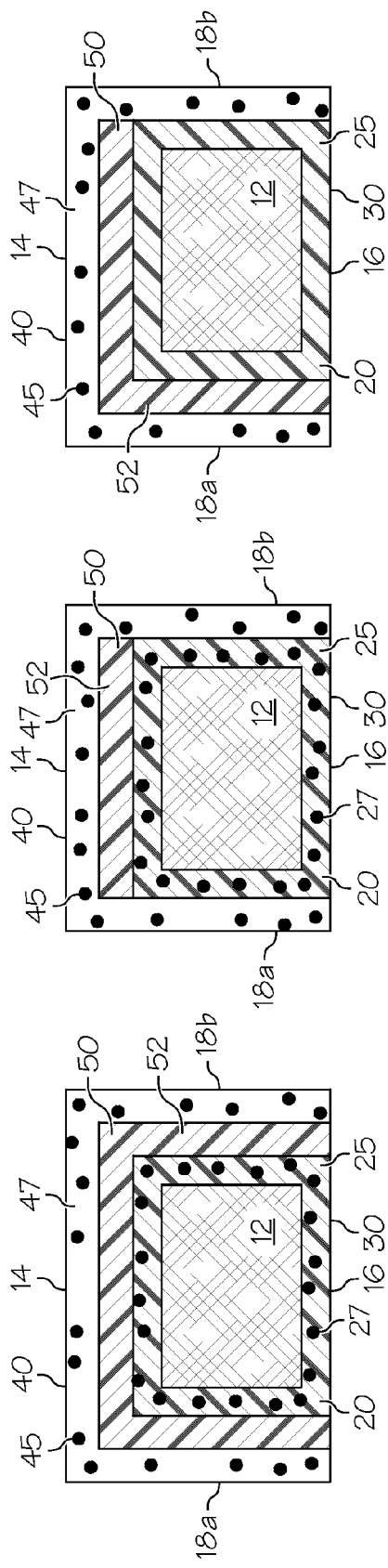

FIGS. 4A-4Y show cross-sectional views of embodiments where an inner coating composition 20 is disposed on all surfaces of a stent strut. The inner coating composition 20 disposed on the luminal surface 16 of the strut 12 forms an exposed surface 30. A barrier coating composition 50 is disposed on a portion of the inner coating composition 20. An outer coating composition 40 is disposed on a portion of the barrier coating composition 50.

In the embodiment shown in FIG. 4A, an inner coating composition 20, comprising a first polymer 25, is disposed on the abluminal surface 14, luminal surface 16, first and second side surfaces 18a, 18b and any other surface of the strut 12. The inner coating composition 20 is disposed on all surfaces of the strut 12 thereby encapsulating the strut 12. In alternate embodiments, the barrier coating composition 50 can comprise non-polymeric materials such as metal. The preferred metals are niobium, tantalum, stainless steel, iridium, iridium oxide, platinum, and gold. Preferably, as shown in this figure, the inner coating composition 20 is disposed directly on the strut surfaces so that there is no intervening material between the inner coating composition 20 and the strut surfaces. Also, in this embodiment, the inner coating composition 20 comprises a therapeutic agent 27. In alternative embodiments, the inner coating composition 20 can be free of a therapeutic agent when applied onto strut surfaces. In addition, as shown in FIG. 4A, the inner coating composition 20 that is disposed on the luminal surface 14 of the strut 12 forms an exposed surface 30 that is not covered by another coating composition.

Also, in FIG. 4A, a barrier coating composition 50, which comprises a second polymer 52, is disposed on portions of the inner coating composition 20 that are disposed on the abluminal surface 14 and the first and second side surfaces 18a, 18b of the strut 12. Preferably, as shown in this figure, the barrier coating composition 50 is disposed directly on the inner coating composition 20 so that there is no intervening material between the inner and barrier coating compositions 20, 50. The barrier coating composition 50 can be disposed on the inner coating composition 20 such that only a part of or the entire inner coating composition 20 disposed on each of these surfaces is covered by the barrier coating composition 50.

An outer coating composition 40, which comprises a third polymer 47 and a second therapeutic agent 45, is disposed on portions of the barrier coating composition 50 that are disposed on the portions of the inner coating composition 20 that is disposed on the abluminal surface 14 and the first and second side surfaces 18a, 18b of the strut 12. Preferably, as shown in this figure, the outer coating composition 40 is disposed directly on the barrier coating composition 50 so that there is no intervening material between the barrier and the outer coating compositions 50, 40. The outer coating composition 40 can be disposed on the barrier coating composition 50 such that only a part of or the entire barrier coating composition 50 is covered by the outer coating composition 40. The second therapeutic agent 47 can be the same or different from the first therapeutic agent 27. Preferably, the second therapeutic agent 45 is one for treating the body lumen wall, such as an anti-restenosis agent. Furthermore, one or more of the first polymer 25, second polymer 52 and third polymer 47 can be the same or different.

As shown in FIG. 4A, the barrier coating composition 50 provides a separation between the inner coating composition 20 and the outer coating composition 40. The barrier coating composition 50 prevents undesired migration of therapeutic agent between coating compositions. In some embodiments, if therapeutic agent was to migrate between the inner coating composition 20 and the outer coating composition 40, it may become trapped in the outer coating composition 40 and thus is not available for elution to the blood vessel or the lumen. Furthermore, in cases where a different therapeutic agent is located in the inner coating composition 20 and the outer coating composition 40, it can be preferable the therapeutic agent in the outer coating composition 40 be delivered to the blood vessel wall, and the therapeutic agent in the inner coating composition 20 be delivered to the lumen. Without the barrier coating composition 50, there may be risk of migration of therapeutic agent across the compositions and into either the blood vessel wall or the lumen, thus potentially resulting in therapeutic agent meant for the lumen delivered to the blood vessel wall or therapeutic agent meant for the blood vessel wall delivered to the lumen.

The embodiments shown in FIGS. 4B-4E are similar to that shown in FIG. 4A except that the barrier coating composition 50 is not disposed on portions of the inner coating composition 20 that is disposed on the abluminal surface 14 as well as portions disposed on both side surfaces 18a, 18b of the strut 12. Also, in the embodiments shown in FIGS. 4B-4E, the outer coating composition 40 is disposed on both the portions of the inner and/or barrier coating composition that are disposed on the abluminal surface 14 as well as both side surfaces 18a, 18b.

FIG. 4B shows an embodiment where the barrier coating composition 50 is only disposed on the portion of the inner coating composition 20 that is disposed on the abluminal surface 14.

In FIG. 4C, the barrier coating composition 50 is only disposed on a portion of the inner coating composition 20 that is disposed on the abluminal surface 14 and on a portion of the inner coating composition 20 that is disposed on one of the side surfaces 18a. The barrier coating composition 50 is not disposed on the inner coating composition 20 that is disposed on the other side surface 18b. Alternatively, the barrier coating composition 50 can be disposed on the inner coating composition 20 that is disposed on side surface 18b instead of that disposed on side surface 18a.

Figure 4E:
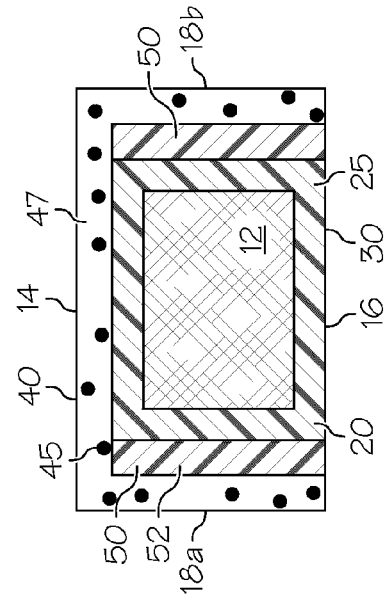
Figure 4D:
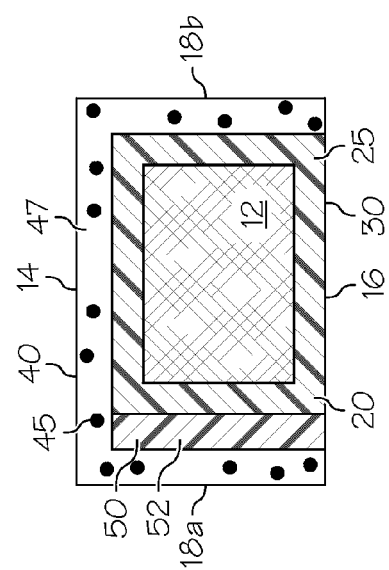
Figure 4F:
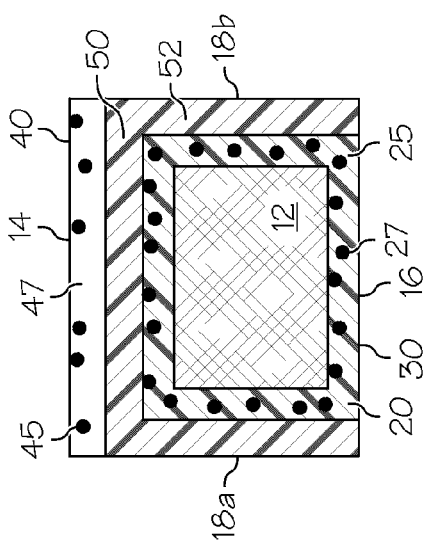
Figure 4G:
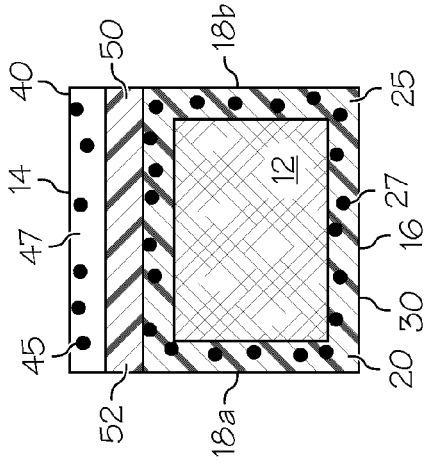
Figure 4H:
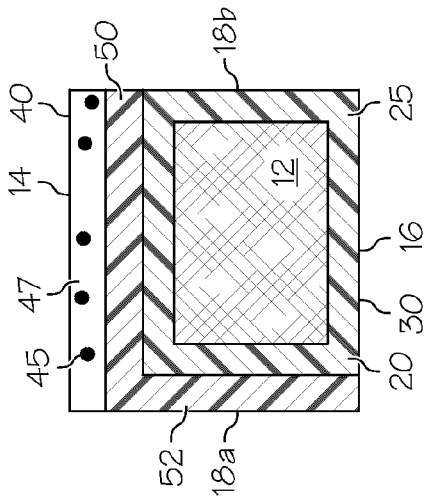
Figure 4I:
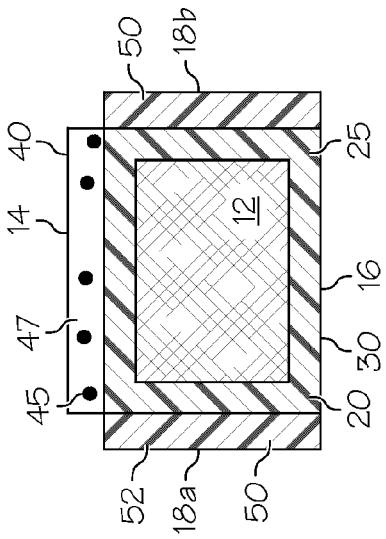
Figure 4J:
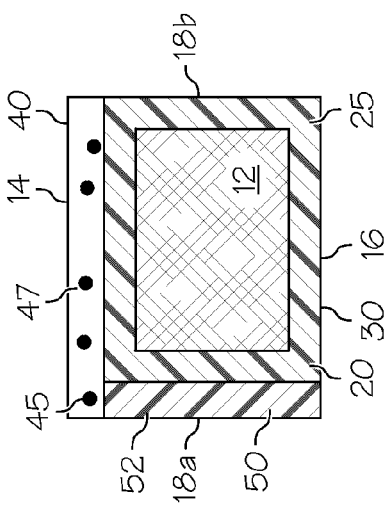

FIG. 4D shows an embodiment where the barrier coating composition 50 is only disposed on a portion of the inner coating composition 20 that is disposed on one of the side surfaces 18a. The barrier coating composition 50 is not disposed on the inner coating composition 20 that is disposed on the abluminal surface 14 or the other side surface 18b. Alternatively, the barrier coating composition 50 can be disposed on the inner coating composition 20 that is disposed on side surface 18b instead of that disposed on side surface 18a. Also, as shown in FIG. 4E, the barrier coating composition 50 can be disposed on both portions of the inner coating composition 20 that is disposed on both side surfaces 18a, 18b but not on the portion of the inner coating-composition 20 disposed on the abluminal surface 14.

FIGS. 4F-4J show embodiments in which the inner coating composition 20 and the barrier coating composition 50 are disposed in a manner similar to the respective embodiments shown in FIGS. 4A-4E. However, in the embodiments shown in FIGS. 4F-4J, the outer coating composition 40 is disposed only on the portions of the inner and/or barrier coating composition that are disposed on the abluminal surface 14.

FIGS. 4K-4O show embodiments in which the inner coating composition 20 and the barrier coating composition 50 are disposed in a manner similar to the respective embodiments shown in FIGS. 4A-4E. However, in the embodiments shown in FIGS. 4K-4O, the outer coating composition 40 is disposed on the portions of the inner and/or barrier coating composition that are disposed on the abluminal surface 14 and only one of the side surfaces 18a. Alternatively, the outer coating composition 40 can be disposed on the portions of the inner and/or barrier coating composition that are disposed on side surface 18b instead of side surface 18a.

FIGS. 4P-4T show embodiments in which the inner coating composition 20 and the barrier coating composition 50 are disposed in a manner similar to the respective embodiments shown in FIGS. 4A-4E. However, in the embodiments shown in FIGS. 4P-4T, the outer coating composition 40 is disposed only on the portions of the inner and/or barrier coating composition that are disposed on one of the side surfaces 18a. Alternatively, the outer coating composition 40 can be disposed on the portions of the inner and/or barrier coating composition that are disposed on side surface 18b instead of side surface 18a.

FIGS. 4U-4Y show embodiments in which the inner coating composition 20 and the barrier coating composition 50 are disposed in a manner similar to the respective embodiments shown in FIGS. 4A-4E. However, in the embodiments shown in FIGS. 4U-4Y, the outer coating composition 40 is disposed only on the portions of the inner and/or barrier coating composition that are disposed on both side surfaces 18a, 18b but not on the portions of the inner and/or barrier coating composition that are disposed on the abluminal surface 14.

Figure 5:
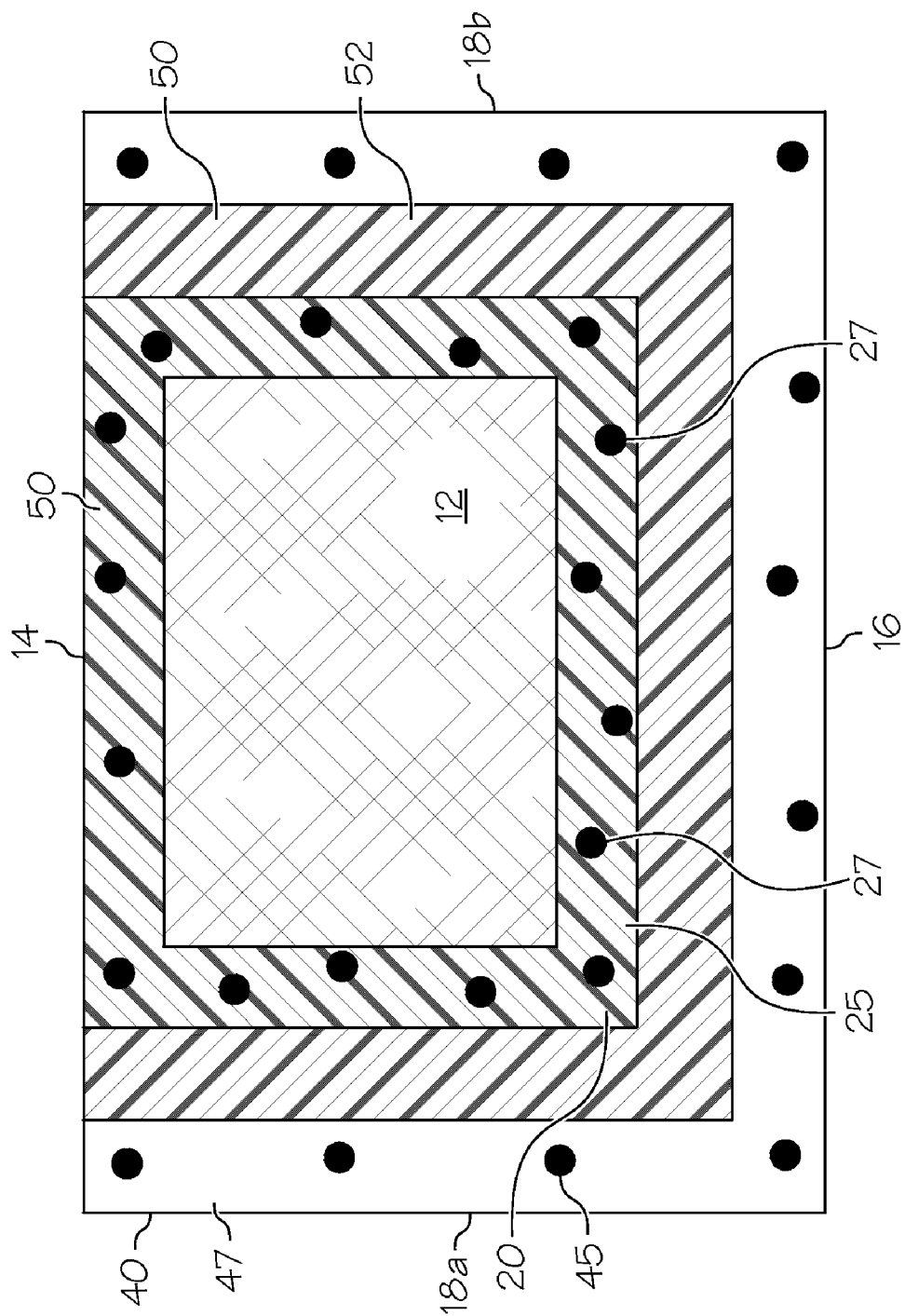
FIG. 5 shows a cross-sectional view of another embodiments of a stent strut having an inner coating composition, barrier coating composition and an outer coating composition disposed on one or more of the strut surfaces.

Although FIGS. 4A-4Y show embodiments having a barrier composition where the inner coating composition disposed on the luminal surface of the strut comprises an exposed surface, in alternative embodiments, the inner coating composition disposed on the abluminal surface of the strut can comprise an exposed surface. FIG. 5 shows such an embodiment. Specifically, this embodiment comprises a inner coating composition 20, comprising a first polymer 25 disposed on the abluminal surface 14, luminal surface 16, first and second side surfaces 18a, 18b and any other surface of the strut 12. The inner coating composition 20 is disposed on all surfaces of the strut 12 thereby encapsulating the strut 12.

Preferably, as shown in this figure, the inner coating composition 20 is disposed directly on the strut surfaces so that there is no intervening material between the inner coating composition 20 and the strut surfaces. Also, in this embodiment, the inner coating composition 20 comprises a therapeutic agent 27. In alternative embodiments, the inner coating composition 20 can be free of a therapeutic agent when applied onto the strut surfaces. In addition, as shown in FIG. 5, the inner coating composition 20 that is disposed on the abluminal surface 16 of the strut 12 forms an exposed surface 30 that is not covered by another coating composition.

Also, in FIG. 5, a barrier coating composition 50, which comprises a second polymer 52, is disposed on portions of the inner coating composition 20 that are disposed on the luminal surface 16 and the first and second side surfaces 18a, 18b of the strut 12. In alternative embodiments, the barrier coating composition 50 comprises non-polymeric materials such as metal. Preferably, as shown in this figure, the barrier coating composition 50 is disposed directly on the inner coating composition 20 so that there is no intervening material between the inner and barrier coating compositions 20, 50. The barrier coating composition 50 can be disposed on the inner coating composition 20 such that only a part of or the entire inner coating composition 20 disposed on each of these surfaces is covered by the barrier coating composition 50.

An outer coating composition 40, which comprises a third polymer 47 and a second therapeutic agent 45, is disposed on portions of the barrier coating composition 20 that are disposed on the portions of the inner coating composition 20 that is disposed on the luminal surface 16 and the first and second side surfaces 18a, 18b of the strut 12. Preferably, as shown in this figure, the outer coating composition 40 is disposed directly on the barrier coating composition 50 so that there is no intervening material between the outer and barrier coating compositions 40, 50. The outer coating composition 40 can be disposed on the barrier coating composition 50 such that only a part of or the entire barrier coating composition 50 is covered by the outer coating composition 40. The second therapeutic agent 47 can be the same or different from the first therapeutic agent 27. Preferably, the second therapeutic agent 45 is one for delivery to a body fluid, such as the blood. Furthermore, one or more of the first polymer 25, second polymer 52 and third polymer 47 can be the same or different. The embodiment shown in FIG. 5 can have variations to its coating compositions such as those described in FIGS. 4B and 4Y.

A. Medical Devices

Medical devices that are particularly suitable for the present invention include stents for various medical purposes. Preferably, the stents are intravascular stents that are designed for implantation in a blood vessel of a patient. Suitable intravascular stents include self-expanding stents and balloon expandable stents. Examples of self expanding stents useful in the present invention are illustrated in U.S. Pat. Nos. 4,655,771 and 4,954,126 issued to Wallsten and 5,061,275 issued to Wallsten et al. Examples of suitable balloon expandable stents are shown in U.S. Pat. No. 5,449,373 issued to Pinchasik et al. In certain embodiments, the stent comprises a sidewall stent structure comprising struts and openings. When such stents are used, it is in some instances preferable to have the coating disposed on the stent to conform to the struts to preserve the openings of the sidewall structure. In preferred embodiments, the stent suitable for the present invention is an Express stent. More preferably, the Express stent is an Express™ stent or an Express2™ stent (Boston Scientific, Inc. Natick, Mass.).

Stents that are suitable for the present invention may be fabricated from metallic, ceramic, polymers, or a combination thereof. Preferably, the materials are biocompatible. Metallic material is more preferable. Suitable metallic materials include metals and alloys based on titanium (such as nitinol, nickel titanium alloys, thermo memory alloy materials), stainless steel, tantalum, nickel chrome, or certain cobalt alloys including cobalt chromium nickel alloys such as Elgiloy® and Phynox®. Metallic materials also include clad composite filaments, such as those disclosed in WO 94/16646.

Suitable ceramic materials include, but are not limited to, oxides, carbides, or nitrides of the transition elements such as titanium oxides, hafnium oxides, iridiumoxides, chromium oxides, aluminum oxides, and zirconiumoxides. Silicon based materials, such as silica, may also be used.

Polymers may be used for forming the stent in the present invention include without limitation biostable or bioabsorbable polymers. Examples include isobutylene-based polymers, polystyrene-based polymers, polyacrylates, and polyacrylate derivatives, vinyl acetate-based polymers and its copolymers, polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for forming stents include without limitation dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(γ-caprolactone), poly(γ-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

Stents may also be made with non-polymers. Examples of useful non-polymers include sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymers include cholesterol, glyceryl monostearate, glycerol tristearate, stearic acid, stearic anhydride, glyceryl monooleate, glyceryl monolinoleate, and acetylated monoglycerides.

B. Suitable Therapeutic Agents

The term "therapeutic agent" encompasses biologically active materials, and also genetic materials and biological materials. The therapeutic agents named herein include their analogs and derivatives. Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), pimecrolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti-thrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, paclitaxel (as well as its derivatives, analogs or paclitaxel bound to proteins, e.g. Abraxane™) 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl)glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In one embodiment, the therapeutic agent is a smooth muscle cell inhibitor or antibiotic. In a preferred embodiment, the therapeutic agent is taxol (e.g., Taxol®), or its analogs or derivatives. In another preferred embodiment, the therapeutic agent is paclitaxel, or its analogs or derivatives. In yet another preferred embodiment, the therapeutic agent is an antibiotic such as erythromycin, amphotericin, rapamycin, adriamycin, etc.

The term "genetic materials" means DNA or RNA, including, without limitation, of DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;

anti-inflammatory agents such as glucocorticoids, betamethasone, dexamethasone, prednisolone, corticosterone, budesonide, estrogen, sulfasalazine, rosiglitazone, mycophenolic acid and mesalamine; anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives;

anesthetic agents such as lidocaine, bupivacaine, and ropivacaine;

anti-coagulants such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;

DNA demethylating drugs such as 5-azacytidine, which is also categorized as a RNA or DNA metabolite that inhibit cell growth and induce apoptosis in certain cancer cells;

vascular cell growth promoters such as growth factors, vascular endotbelial growth factors (VEGF, all types including VEGF-2), growth factor receptors, transcriptional activators, and translational promoters;

vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents, vasodilating agents, and agents which interfere with endogenous vasoactive mechanisms;

anti-oxidants, such as probucol;

antibiotic agents, such as penicillin, cefoxitin, oxacillin, tobranycin, rapamycin (sirolimus);

angiogenic substances, such as acidic and basic fibroblast growth factors, estrogen including estradiol (E2), estriol (E3) and 17-beta estradiol;

drugs for heart failure, such as digoxin, beta-blockers, angiotensin-converting enzyme (ACE) inhibitors including captopril and enalopril, statins and related compounds; and macrolide agents such as sirolimus, pimecrolimus, tacrolimus, zotarolimus or everolimus.

Preferred therapeutic agents include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other suitable therapeutic agents include tacrolimus; halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins.

Other preferred therapeutic agents include nitroglycerin, nitrous oxides, nitric oxides, aspirins, digitalis, estrogen derivatives such as estradiol and glycosides.

In one embodiment, the therapeutic agent is capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In another embodiment, the therapeutic agent is capable of inhibiting cell proliferation and/or migration.

In certain embodiments, the therapeutic agents for use in the medical devices of the present invention can be synthesized by methods well known to one skilled in the art. Alternatively, the therapeutic agents can be purchased from chemical and pharmaceutical companies.

C. Suitable Polymers

Polymers useful for forming the coating compositions should be ones that are biocompatible, particularly during insertion or implantation of the device into the body and avoids irritation to body tissue. They can include biostable or bioabsorbable polymers. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. The polymer may be selected to allow the coating to better adhere to the surface of the strut when the stent is subjected to forces or stress. Furthermore, although the coating can be formed by using a single type of polymer, various combinations of polymers can be employed.

Generally, when a hydrophilic therapeutic agent is used then a hydrophilic polymer having a greater affinity for the therapeutic agent than another material that is less hydrophilic is preferred. When a hydrophobic therapeutic agent is used then a hydrophobic polymer having a greater affinity for the therapeutic agent is preferred.

Examples of suitable hydrophobic polymers or monomers include, but not limited to, polyolefins, such as polyethylene, polypropylene, poly(1-butene), poly(2-butene), poly(1-pentene), poly(2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3, 3-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly (vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly (n-butyl acetate), poly(ethyl acrylate), poly(1-chlorodifluoromethyl)tetrafluoroethyl acrylate, poly di(chlorofluoromethyl)fluoromethyl acrylate, poly(1,1-dihydroheptafluorobutyl acrylate), poly(1,1-dihydropentafluoroisopropyl acrylate), poly(1,1-dihydropentadecafluorooctyl acrylate), poly (heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly (ethylene terephthalate) and poly(butylene terephthalate); condensation type polymers such as and polyurethanes and siloxane-urethane copolymers; polyorganosiloxanes, i.e., polymeric materials characterized by repeating siloxane groups, represented by Ra SiO 4-a/2, where R is a monovalent substituted or unsubstituted hydrocarbon radical and the value of a is 1 or 2; and naturally occurring hydrophobic polymers such as rubber.

Examples of suitable hydrophilic polymers or monomers include, but not limited to; (meth)acrylic acid, or alkaline metal or ammonium salts thereof; (meth)acrylamide; (meth) acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl (meth)acrylate and 2-hydroxypropyl(meth)acrylate.

Polyvinyl alcohol is also an example of hydrophilic polymer. Polyvinyl alcohol may contain a plurality of hydrophilic groups such as hydroxyl, amido, carboxyl, amino, ammonium or sulfonyl (—SO3). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

Preferably, for stents which undergo mechanical challenges, e.g., expansion and contraction, polymers should be selected from elastomeric polymers such as silicones (e.g., polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition is capable of undergoing deformation under the yield point when the device is subjected to forces, stress or mechanical challenge.

D. Methods for Making the Coatings

The coating compositions can be prepared by dissolving or suspending a polymer and/or therapeutic agent in a solvent. Solvents that may be used to prepare coating compositions include ones which can dissolve or suspend the polymer and/or therapeutic agent in solution. Examples of suitable solvents include, but are not limited to, tetrahydrofuran, methylethylketone, chloroform, toluene, acetone, isooctane, 1,1,1, trichloroethane, dichloromethane, isopropanol, IPA, and mixtures thereof.

The aforementioned coated medical devices can be made by applying coating compositions onto the surface of the medical device. Coating compositions can be applied by any method to a surface of a medical device or to another coating composition known by one skilled in the art. The different surfaces may be coated by the same or different methods. Suitable methods for applying the coating compositions to the medical devices include, but are not limited to, spray-coating, painting, rolling, electrostatic deposition, ink jet coating, and a batch process such as air suspension, pan-coating or ultrasonic mist spraying, or a combination thereof.

In embodiments where a coating composition is to be applied to fewer than all the surfaces of the struts of a stent, such as on the stents described above, it is preferable to employ coating methods that selectively apply the coating composition. For instance, a coating composition can be deposited onto a substrate. The substrate is preferably made from materials that has minimal adhesion the coating composition so that the coating composition can be easily removed and transferred to the surfaces of the struts. Then, the abluminal surface 14 and side surfaces 18*a*, 18*b* of the struts may be rolled over the coated substrate to transfer the coating composition to these surfaces.

Also, it may be preferable to mask or cover the surface that is not to be coated with a particular coating composition. For instance to avoid having a coating composition disposed upon the luminal surface 16 of the strut 12, the luminal surface 16 can be masked.

The luminal surface 16 can be masked, for instance, by application of a protective wrap to that surface. The protective wrap is a material that would protect the coated surface from exposure to the coating applied to the opposing surface. Suitable material for this protective wrap include, for example, PTFE film, dyna-leap, Kaptont, or any other appropriate type of covering or wrapping material. The protective wrap preferably extends for the length of the stent, and is secured so that it does not unwrap. The protective wrap serves to protect the luminal surface 16 from exposure to the coating composition as it is being applied to other surfaces of the strut. For instance, the protective wrap will protect a luminal surface 16 that has been already coated from additional deposition of another coating composition that is being applied to the other strut surfaces. After the other surfaces have been coated, the wrap covering the luminal surface 16 may be removed.

In one embodiment, the luminal surface 16 can be masked by placing the stent 10 on a mandrel. The luminal surface 16 which is placed against the mandrel will not be exposed to a coating composition that is applied to the abluminal surface 14. For example, in an embodiment, the stent that is mounted on the mandrel may then be rolled over a substrate containing a coating composition to transfer the coating composition to the abluminal surface 14 and side surfaces 18*a*, 18*b*. Alternatively, the stent 10 can be placed on the mandrel 50 and the abluminal surface 14 and side surfaces 18*a*, 18*b* of the strut 12 are spray-coated with the coating composition 40. Another method of masking the adluminal surface 16 includes placing a tube inside the stent 10 and inflating the tube so that it acts as a seal against the stent 10. Then, the coating composition can be deposited on the abluminal surface 15 and side surfaces 18*a*, 18*b* of the stent 10 by any number of methods including spray coating, dipping, rolling, or other known means. An alternative approach to selectively coating the stent 10 is to coat specified areas of the stent strut 12 via ink jet coating, roller coating, or other similar means.

For spray coating, a nozzle assembly may be used to spray a coating composition onto the luminal surface. The nozzle assembly may be in the form of a cone that sprays the coating composition at an angle. The angle of the spray from the nozzles may need to be adjusted to ensure uniform thickness of the coating on the luminal surface. Also, a nozzle assembly with small spray nozzles can be inserted into one end of the stent and moved through the stent until it extends past the opposite end of the stent. Preferably, the spray mist flow is started while the nozzle is still outside of the stent. This step places a coating composition on the luminal surface and one side surface of the struts of the stent. The coating process may be repeated again. Preferably, the spray nozzle is inserted into the other end of the stent to coat the other side surface of the struts. By repeating the spraying from two directions, both side surfaces are coated with a coating composition.

After a coating composition has been applied, it can be cured. Curing is defined as the process of converting the polymeric material into the finished or useful state by the application of heat, vacuum, and/or chemical agents which induce physico-chemical changes. The applicable time and temperature for curing are determined by the particular polymer involved and particular therapeutic agent used, if any, as known by one skilled in the art. The coated medical devices may thereafter be subjected to a post-cure process wherein the medical devices are exposed to a low energy for stabilization of the coating. Also, after the medical device is coated, it preferably should be sterilized by methods of sterilization as known in the art.

In use, a coated medical device, such as an expandable stent, according to the present invention can be made to provide desired release profile of the therapeutic agent. The medical devices and stents of the present invention may be used for any appropriate medical procedure. Delivery of the medical device can be accomplished using methods well known to those skilled in the art, such as mounting the stent on an inflatable balloon disposed at the distal end of a delivery catheter.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A stent for implantation in a body lumen of a patient comprising:
    a stent sidewall structure comprising a plurality of struts in which at least one strut has an abluminal surface, a luminal surface opposite the abluminal surface, a first side surface, and a second side surface opposite the first side surface, in which the first and second side surface are each adjacent to and connect the abluminal surface and the luminal surface;
    an inner coating composition comprising a first polymer disposed on the abluminal surface, luminal surface, first and second side surfaces and any other surface of the strut such that the inner coating composition is disposed on all surfaces of the strut; wherein the inner coating composition is free of any therapeutic agent when applied onto the surfaces of the strut; and wherein the inner coating composition that is disposed on the luminal surface forms an exposed surface; and
    an outer coating composition disposed on at least a portion of the inner coating composition that is disposed on at least one of the abluminal surface or first side surface or second side surface, wherein the luminal surface is free of the outer coating composition; wherein the outer coating composition comprises a first therapeutic agent and the first polymer.

2. The stent of claim 1, wherein the inner coat composition is disposed directly on all the surfaces of the strut.

3. The sent of claim 1, wherein the outer coating composition is disposed directly on the inner coating composition.

4. The stent of claim 1, wherein the outer coating composition is disposed on at least a portion of the inner coating composition that is disposed on the abluminal surface and on at least a portion of the inner coating composition disposed on the first side surface or the second side surface.

5. The stent of claim 4, wherein the outer coating composition is disposed on at least portions of the inner coating composition that are disposed on the first and second side surfaces.

6. The stent of claim 1, wherein the first therapeutic agent comprises an anti-thrombogenic agent, anti-angiogensis agent, anti-proliferative agent, anti-restenosis agent, growth factor or radiochemical.

7. The stent of claim 1, wherein the first therapeutic agent comprises paclitaxel, sirolimus, everolimus, pimerolimus, tacrolimus, or zotarolimus.

8. An intravascular stent for implantation in a blood vessel of a patient comprising:
    a stent sidewall structure comprising a plurality of struts in which at least one strut has an abluminal surface, a luminal surface opposite the abluminal surface, a first side surface, and a second side surface opposite the first side surface, in which the first and second side surfaces are each adjacent to and connect the abluminal surface and the luminal surface;
    an inner coating composition comprising a first biostable polymer disposed directly on the abluminal surface, luminal surface, first and second side surfaces and any other surface of the strut such that the inner coating composition is disposed directly on all surfaces of the strut; wherein the inner coating composition is free of any therapeutic agent when applied onto the surfaces of the strut; and wherein the inner coating composition that is disposed on the luminal surface forms an exposed surface; and
    an outer coating composition disposed on at least a portion of the inner coating composition that is disposed on the abluminal surface and on at least portions of the inner coating composition that are disposed on the first and second side surfaces, wherein the luminal surface is free of the outer coating composition; wherein the outer coating composition comprises an anti-restenosis agent and the first polymer.

* * * * *